US010658069B2

(12) United States Patent
Conway et al.

(10) Patent No.: US 10,658,069 B2
(45) Date of Patent: *May 19, 2020

(54) BIOLOGICAL SEQUENCE VARIANT CHARACTERIZATION

(71) Applicant: International Business Machines Corporation, Armonk, NY (US)

(72) Inventors: Thomas C. Conway, Melbourne (AU); Kelly L Wyres, Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 854 days.

This patent is subject to a terminal disclaimer.

(21) Appl. No.: 14/511,829

(22) Filed: Oct. 10, 2014

(65) Prior Publication Data

US 2016/0103954 A1 Apr. 14, 2016

(51) Int. Cl.
*G16B 30/00* (2019.01)
*G16B 20/00* (2019.01)

(52) U.S. Cl.
CPC ............. *G16B 30/00* (2019.02); *G16B 20/00* (2019.02)

(58) Field of Classification Search
None
See application file for complete search history.

(56) References Cited

U.S. PATENT DOCUMENTS

| 7,563,572 | B2 | 7/2009 | Pont-Kingdon et al. |
| 7,575,864 | B2 | 8/2009 | Bedzyk et al. |
| 8,775,428 | B2 | 7/2014 | Birdwell et al. |
| 2012/0149593 | A1 | 6/2012 | Hicks et al. |
| 2012/0172237 | A1 | 7/2012 | Ding et al. |
| 2012/0264621 | A1 | 10/2012 | Hubbell et al. |
| 2013/0225419 | A1 | 8/2013 | Chasin et al. |
| 2014/0186827 | A1 | 7/2014 | Pieprzyk et al. |

FOREIGN PATENT DOCUMENTS

| WO | 2013062856 A1 | 5/2013 |
| WO | 2013138510 A9 | 9/2013 |

OTHER PUBLICATIONS

Boisvert ete al Genome Biology 2012.*
Morgulis et al Bioinformatics vol. 24 No. 16 1757-1764 2008.*
Simpson et al. Genome Res 19 1117-1123 2009.*
Nagarajan et al. Sequence assembly demystified Nature Reviews vol. 14 pp. 157-167 (Year: 2013).*
Nagarajan et al. Sequence assembly demystified Nature Reviews Genetics vol. 14, pp. 157-167 (Year: 2013).*
Flicek et al. Sense from sequence reads: methods for alignment and assembly Nature Methods Supplement vol. 6 pp. S6-S12 (Year: 2009).*

I.H. Yildirim et al., "Molecular Methods for Bacterial Genotyping and Analyzed Gene Regions," Journal of Microbiology and Infectious Diseases (JMID), Jun. 2011, pp. 42-46, vol. 1, No. 1.
C. Jaing et al., "Report for Development of a Census Array and Evaluation of the Array to Detect Biothreat Agents and Environmental Samples for DHS," Lawrence Livermore National Laboratory (LLNL), LLNL-TR-480650, Jan. 2011, 11 pages.
J. Versalovic et al., "Genomic Fingerprinting of Bacteria Using Repetitive Sequence-Based Polymerase Chain Reaction," Methods in Molecular and Cellular Biology, May 1994, pp. 25-40, vol. 5.
J. Blażewicz et al., "Selected Combinatorial Problems of Computational Biology," European Journal of Operational Research, Mar. 2005, pp. 585-597, vol. 161.
B. Hu et al., "Pathogen Comparative Genomics in the Next-Generation Sequencing Era: Genome Alignments, Pangenomics and Metagenomics," Briefings in Functional Genomics, Nov. 2011, pp. 322-333, vol. 10, No. 6.
F.A. Matsen et al., "pplacer: Linear Time Maximum-Likelihood and Bayesian Phylogenetic Placement of Sequences Onto a Fixed Reference Tree," BMC Bioinformatics, Oct. 2010, pp. 538-555, vol. 11, No. 1.
J. Kim et al., "Reference-Assisted Chromosome Assembly," Proceedings of the National Academy of Sciences, Jan. 2013, pp. 1785-1790, vol. 110, No. 5.
C. Titus Brown, "BIGDATA: Small: DA: DCM: Low-Memory Streaming Prefilters for Biological Sequencing Data," DCM, Jul. 2012, 21 pages.
P. Keim et al., "Multiple-Locus Variable-Number Tandem Repeat Analysis Reveals Genetic Relationships with Bacillus Anthracis," Journal of Bacteriology, May 2000, pp. 2928-2936, vol. 182, No. 10.
M.C.J. Maiden et al., "Multilocus Sequence Typing: A Portable Approach to the Identification of Clones Within Populations of Pathogenic Microorganisms," Proceedings of the National Academy of Sciences, Mar. 1998, pp. 3140-3145, vol. 95.
K.L. Wyres et al., "The Multidrug-Resistant PMEN1 Pneumococcus is a Paradigm for Genetic Success," Genome Biology, Nov. 2012, 12 pages, vol. 13, No. 11.
M. Murphy et al., "Development and Application of Multiple-Locus Variable Number of Tandem Repeat Analysis (MLVA) to Subtype a Collection of Listeria Monocytogenes," International Journal of Food Microbiology, Apr. 2007, pp. 187-194, vol. 115, No. 2.

(Continued)

*Primary Examiner* — John S Brusca
(74) *Attorney, Agent, or Firm* — Joseph Petrokaitis; Ryan, Mason & Lewis, LLP

(57) ABSTRACT

Short fixed length sub-sequences, defined as reference sub-sequences, are extracted from a collection of reference sequences, and an index is constructed showing which short fixed length reference sub-sequence occurs in which reference sequences. Short fixed length sub-sequences, the same length as the reference sub-sequences and defined as source sub-sequences, are extracted from a collection of source sequences derived from a sample for which the signature is to be determined, and the short fixed length source sub-sequences are compiled to determine the frequency of each within the collection. The presence or absence of source sub-sequences in combination with the index is used to infer the presence or absence of reference sequences from the reference collection.

20 Claims, 9 Drawing Sheets

Specification includes a Sequence Listing.

(56) References Cited

OTHER PUBLICATIONS

A.C. Noller et al., "Multilocus Variable-Number Tandem Repeat Analysis Distinguishes Outbreak and Sporadic *Escherichia coli* O157:H7 Isolates," Journal of Clinical Microbiology, Dec. 2003, pp. 5389-5397, vol. 41, No. 12.

B. Raymond et al., "Environmental Factors Determining the Epidemiology and Population Genetic Structure of the Bacillus Cereus Group in the Field," PLoS Pathogens, May 2010, pp. 1-13, vol. 6, No. 5.

M. Inouye et al., "Short Read Sequence Typing (SRST): Multi-Locus Sequence Types from Short Reads," BMC Genomics, Jul. 2012, 7 pages, vol. 13.

M. Inouye et al., "SRST2: Rapid Genomic Surveillance for Public Health and Hospital Microbiology Labs," biorxiv.org, Oct. 2014, 28 pages.

K.A. Jolley et al., "BIGdb: Scalable Analysis of Bacterial Genome Variation at the Population Level," BMC Bioformatics, Dec. 2010, 11 pages, vol. 11.

P.A. Pevzner et al., "Fragment Assembly with Double-Barreled Data," Bioinformatics, Suppl. 1, Apr. 2001, pp. S225-S233, vol. 17.

T.C. Conway et al., "Succinct Data Structures for Assembling Large Genomes," Feb. 2011, pp. 479-486, vol. 27, No. 4.

P.E.C. Compeau et al., "How to Apply de Bruijn Graphs to Genome Assembly," Nature Biotechnology, Nov. 2011, pp. 987-991, vol. 29, No. 11.

J.N. Burton et al., "Species-Level Deconvolution of Metagenome Assemblies with Hi-C-Based Contact Probability Maps," G3, Jul. 2014, pp. 1339-1346, vol. 4, No. 7.

P. Medvedev et al., "Error Correction of High-Throughput Sequencing Datasets with Non-Uniform Coverage," Bioinformatics, 2011, pp. i137-i141, vol. 27.

Michael L. Metzker, "Sequencing Technologies—The Next Generation," Nature Reviews/Genetics, Jan. 2010, pp. 31-46, vol. 11.

\* cited by examiner

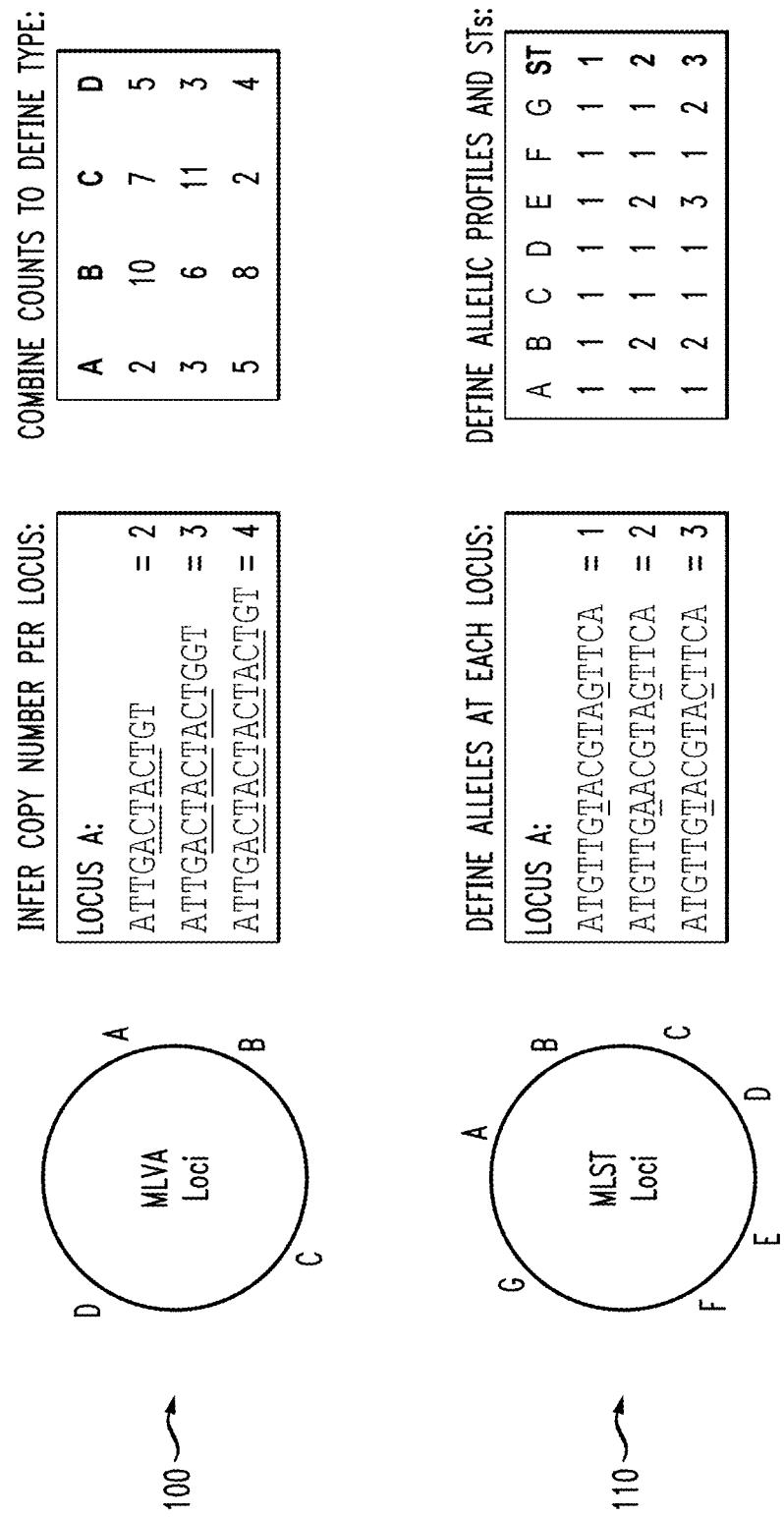

FIG. 2

TRUE SEQUENCE:
ATGCTGGTCATGTCAATGATCGAATGCCCTGGTCATGTAGCTAGCTGGAGTAACTTGTACTGCAG

Sequence reads (210):
```
TGCTGGTCATGTCAA   ATCGAAAGCCCCTGGT ATGTACGACTAGCAGG   TAACTTGTACTGCAG
GCTGGTCATGTCAAT   TCGAATGCCCTGGTC   ACGACTAGCTGGAGT
CTGGTGATGTCAAATG  CGAATGCCCTGGTCA   CGACTAGCTGGAGTA
TGGTCATGTCAATGA   GAATGCCCTGGTCAT   GACTAGCTGGAGTAA
GGTCATGTCAATGAT   AATGCCCTGGTCATG   AGCTGGAGTAACTTG
                  ATGCCCTGGCCATGT
```

COVERAGE DEPTH 220

SEQUENCE READ 210

200

```
                             SEQUENCE LISTING

<160> NUMBER OF SEQ ID NOS: 22

<210> SEQ ID NO 1
<211> LENGTH: 10
<212> TYPE: DNA
<213> ORGANISM: Artificial Sequence
<220> FEATURE:
<223> OTHER INFORMATION: Example sequence fragment

<400> SEQUENCE: 1
aacgcttcga                                                          10

<210> SEQ ID NO 2
<211> LENGTH: 10
<212> TYPE: DNA
<213> ORGANISM: Artificial Sequence
<220> FEATURE:
<223> OTHER INFORMATION: Example sequence fragment

<400> SEQUENCE: 2
tcgaagcgtt                                                          10

<210> SEQ ID NO 3
<211> LENGTH: 11
<212> TYPE: DNA
<213> ORGANISM: Artificial Sequence
<220> FEATURE:
<223> OTHER INFORMATION: Example fragment sequence

<400> SEQUENCE: 3
aacgcttacg a                                                        11

<210> SEQ ID NO 4
<211> LENGTH: 12
<212> TYPE: DNA
<213> ORGANISM: Artificial Sequence
<220> FEATURE:
<223> OTHER INFORMATION: Example sequence fragment

<400> SEQUENCE: 4
attgactact gt                                                       12

<210> SEQ ID NO 5
<211> LENGTH: 16
<212> TYPE: DNA
<213> ORGANISM: Artificial Sequence
<220> FEATURE:
<223> OTHER INFORMATION: Example sequence fragment

<400> SEQUENCE: 5
attgactact actggt                                                   16

<210> SEQ ID NO 6
<211> LENGTH: 18
<212> TYPE: DNA
<213> ORGANISM: Artificial Sequence
<220> FEATURE:
<223> OTHER INFORMATION: Example sequence fragment
```

```
<400> SEQUENCE: 6
attgactact actactgt                                                  18

<210> SEQ ID NO 7
<211> LENGTH: 17
<212> TYPE: DNA
<213> ORGANISM: Artificial Sequence
<220> FEATURE:
<223> OTHER INFORMATION: Example sequence fragment

<400> SEQUENCE: 7
atgttgtacg tagttca                                                   17

<210> SEQ ID NO 8
<211> LENGTH: 17
<212> TYPE: DNA
<213> ORGANISM: Artificial Sequence
<220> FEATURE:
<223> OTHER INFORMATION: Example sequence fragment

<400> SEQUENCE: 8
atgttgaacg tagttca                                                   17

<210> SEQ ID NO 9
<211> LENGTH: 17
<212> TYPE: DNA
<213> ORGANISM: Artificial Sequence
<220> FEATURE:
<223> OTHER INFORMATION: Example sequence fragment

<400> SEQUENCE: 9
atgttgtacg tacttca                                                   17

<210> SEQ ID NO 10
<211> LENGTH: 67
<212> TYPE: DNA
<213> ORGANISM: Artificial Sequence
<220> FEATURE:
<223> OTHER INFORMATION: Example sequence fragment

<400> SEQUENCE: 10
atgctggtca tgtcaatgat cgaatgccct ggtcatgtac gactagctgg agtaacttgt    60
actgcag                                                              67

<210> SEQ ID NO 11
<211> LENGTH: 15
<212> TYPE: DNA
<213> ORGANISM: Artificial Sequence
<220> FEATURE:
<223> OTHER INFORMATION: Example sequence fragment

<400> SEQUENCE: 11
agctggagta acttg                                                     15

<210> SEQ ID NO 12
<211> LENGTH: 75
<212> TYPE: DNA
<213> ORGANISM: Artificial Sequence
<220> FEATURE:
<223> OTHER INFORMATION: Example sequence fragment

<400> SEQUENCE: 12
cttatgctga ttcatctcga tccttgatcc tagatcatca tcatcatcat cgattgcatg    60
```
cgtacctggc attta                                                      75

<210> SEQ ID NO 13
<211> LENGTH: 75
<212> TYPE: DNA
<213> ORGANISM: Artificial Sequence
<220> FEATURE:
<223> OTHER INFORMATION: Example sequence fragment

<400> SEQUENCE: 13
gaatacgact aagtagagct aggaactagg atctagtagt agtagtagta gctaacgtac      60
gcatggaccg taaat                                                      75

<210> SEQ ID NO 14
<211> LENGTH: 17
<212> TYPE: DNA
<213> ORGANISM: Artificial Sequence
<220> FEATURE:
<223> OTHER INFORMATION: Example sequence fragment

<400> SEQUENCE: 14
atgttgtacg tagttca                                                    17

<210> SEQ ID NO 15
<211> LENGTH: 17
<212> TYPE: DNA
<213> ORGANISM: Artificial Sequence
<220> FEATURE:
<223> OTHER INFORMATION: Example sequence fragment

<400> SEQUENCE: 15
atgttgaacg tagttca                                                    17

<210> SEQ ID NO 16
<211> LENGTH: 17
<212> TYPE: DNA
<213> ORGANISM: Artificial Sequence
<220> FEATURE:
<223> OTHER INFORMATION: Example sequence fragment

<400> SEQUENCE: 16
atgttgtacg tacttca                                                    17

<210> SEQ ID NO 17
<211> LENGTH: 17
<212> TYPE: DNA
<213> ORGANISM: Artificial Sequence
<220> FEATURE:
<223> OTHER INFORMATION: Example sequence fragment

<400> SEQUENCE: 17
gtcatgctac ggctatg                                                    17

<210> SEQ ID NO 18
<211> LENGTH: 17
<212> TYPE: DNA
<213> ORGANISM: Artificial Sequence
<220> FEATURE:
<223> OTHER INFORMATION: Example sequence fragment

<400> SEQUENCE: 18
gtcatggtac ggctatg                                                    17

<210> SEQ ID NO 19
<211> LENGTH: 17

```
<212> TYPE: DNA
<213> ORGANISM: Artificial Sequence
<220> FEATURE:
<223> OTHER INFORMATION: Example sequence fragment

<400> SEQUENCE: 19
gtcatggtac gtctatg                                                  17

<210> SEQ ID NO 20
<211> LENGTH: 33
<212> TYPE: DNA
<213> ORGANISM: Artificial Sequence
<220> FEATURE:
<223> OTHER INFORMATION: Example sequence fragment

<400> SEQUENCE: 20
aaaggttttt tcgtttaacg ttgtgatcga tcg                                33

<210> SEQ ID NO 21
<211> LENGTH: 39
<212> TYPE: DNA
<213> ORGANISM: Artificial Sequence
<220> FEATURE:
<223> OTHER INFORMATION: Example sequence fragment

<400> SEQUENCE: 21
aaaagggttt tttacgtatt aacgttcgtg aatcgatcg                          39

<210> SEQ ID NO 22
<211> LENGTH: 33
<212> TYPE: DNA
<213> ORGANISM: Artificial Sequence
<220> FEATURE:
<223> OTHER INFORMATION: Example sequence fragment

<400> SEQUENCE: 22
aaacggtttt tccttttacg ttgtgtatca tcg                                33
```

BIOLOGICAL SEQUENCE VARIANT CHARACTERIZATION

CROSS REFERENCE TO RELATED APPLICATION

The present application is related to the concurrently-filed U.S. patent application identified as Ser. No. 14/511,702, and entitled "Biological Sequence Tandem Repeat Characterization," the disclosure of which is incorporated herein by reference in its entirety.

FIELD

The field relates to analysis of biological sequences and, more particularly, to characterization of biological sequences, for example, sequence variants.

REFERENCE TO SEQUENCE LISTING

The Sequence Listing in ASCII electronic format submitted electronically via EFS-web is incorporated herein by reference in its entirety. The Sequence listing file, entitled YOR920140445US1_SEQ_ASCII.txt, was created on Dec. 15, 2014 and is 860 bytes in size.

BACKGROUND

In general, a sequence is an ordered selection of symbols drawn from an alphabet. The positions in a sequence of length n may be numbered from 0 to n−1. Alphabets may include, but are not limited to, the deoxyribonucleic acid (DNA) alphabet (A, C, G, T), the ribonucleic acid (RNA) alphabet (A, C, G, U) and the amino acid alphabet. Sequences that can be represented using such alphabets are called biological sequences (e.g., DNA sequences, RNA sequences, and protein sequences).

DNA and RNA may be double stranded. It is typically (but not necessarily) the case that each source sequence in a set of source sequences (e.g. obtained from a DNA sequencing machine) is arbitrarily derived from one strand or the other. As a consequence, to correctly interpret the set of source sequences, it is necessary to consider for each source sequence, the sequence that would arise from reading the complementary strand. This other sequence is called the reverse complement sequence. It is equivalent to the sequence obtained by reversing the original sequence and replacing each symbol with its complementary symbol. For types of sequence for which reverse complementation is well defined, each symbol in the alphabet will have a complementary symbol (e.g., for DNA, the complements are symmetric: A and T are complementary as are C and G). For example, the reverse complement of the DNA sequence AACGCTTCGA (SEQ ID NO. 1) is TCGAAGCGTT (SEQ ID NO. 2).

Genotypic characterization (genotyping) is an important method for the identification of organisms and the determination of the relationships between them, often using DNA sequence data. Common genotyping techniques include Multiple Locus Variable number tandem repeat Analysis (MLVA) and Multi-Locus Sequence Typing (MLST), which index genetic variation at defined genomic loci (as further explained below) and create multi-locus profiles that are collected in a database. A genome is the entire complement of DNA in a cell, while a locus is a specific position in the genome (e.g., a region encoding a gene or a letter ("base"), coordinate). In the case of bacteria, the domain of life to which these techniques are most commonly applied, the genome includes the chromosome(s) and any phage or plasmid sequences contained within the cell.

Bacteria are haploid organisms, i.e., in the usual state there is only a single copy of each chromosome per cell and therefore, in the majority of cases, only a single copy of each locus (there are exceptions when loci are duplicated on the same chromosome or on a plasmid). In contrast, among non-haploid organisms, there is more than one copy of each chromosome per cell and therefore multiple copies of each locus, e.g., in humans, which are diploid, there are two copies of each chromosome in each normal cell (excluding germ cells and the X/Y chromosomes).

SUMMARY

Embodiments of the invention provide techniques for characterization of biological sequence signatures.

For example, in one embodiment, a method for determining a signature from biological sequence data comprises the following steps. Short fixed length sub-sequences, defined as reference sub-sequences, are extracted from a collection of reference sequences, and an index is constructed showing which short fixed length reference sub-sequence occurs in which reference sequences. Short fixed length sub-sequences, the same length as the reference sub-sequences and defined as source sub-sequences, are extracted from a collection of source sequences derived from a sample for which the signature is to be determined, and the short fixed length source sub-sequences are compiled to determine the frequency of each within the collection. The presence or absence of source sub-sequences in combination with the index is used to infer the presence or absence of reference sequences from the reference collection.

Advantageously, illustrative embodiments provide methodologies for analysis of biological sequences including, but not limited to, identification and typing (e.g., genetic and/or proteomic characterization) of organisms.

These and other objects, features, and advantages of the present invention will become apparent from the following detailed description of illustrative embodiments thereof, which is to be read in connection with the accompanying drawings.

BRIEF DESCRIPTION OF THE DRAWINGS

FIG. 1 shows MLVA and MLST characterization techniques with which one or more embodiments of the invention may be implemented.

FIG. 2 illustrates an example of next-generation sequence sampling with which one or more embodiments of the invention may be implemented.

DETAILED DESCRIPTION

Figure 3:
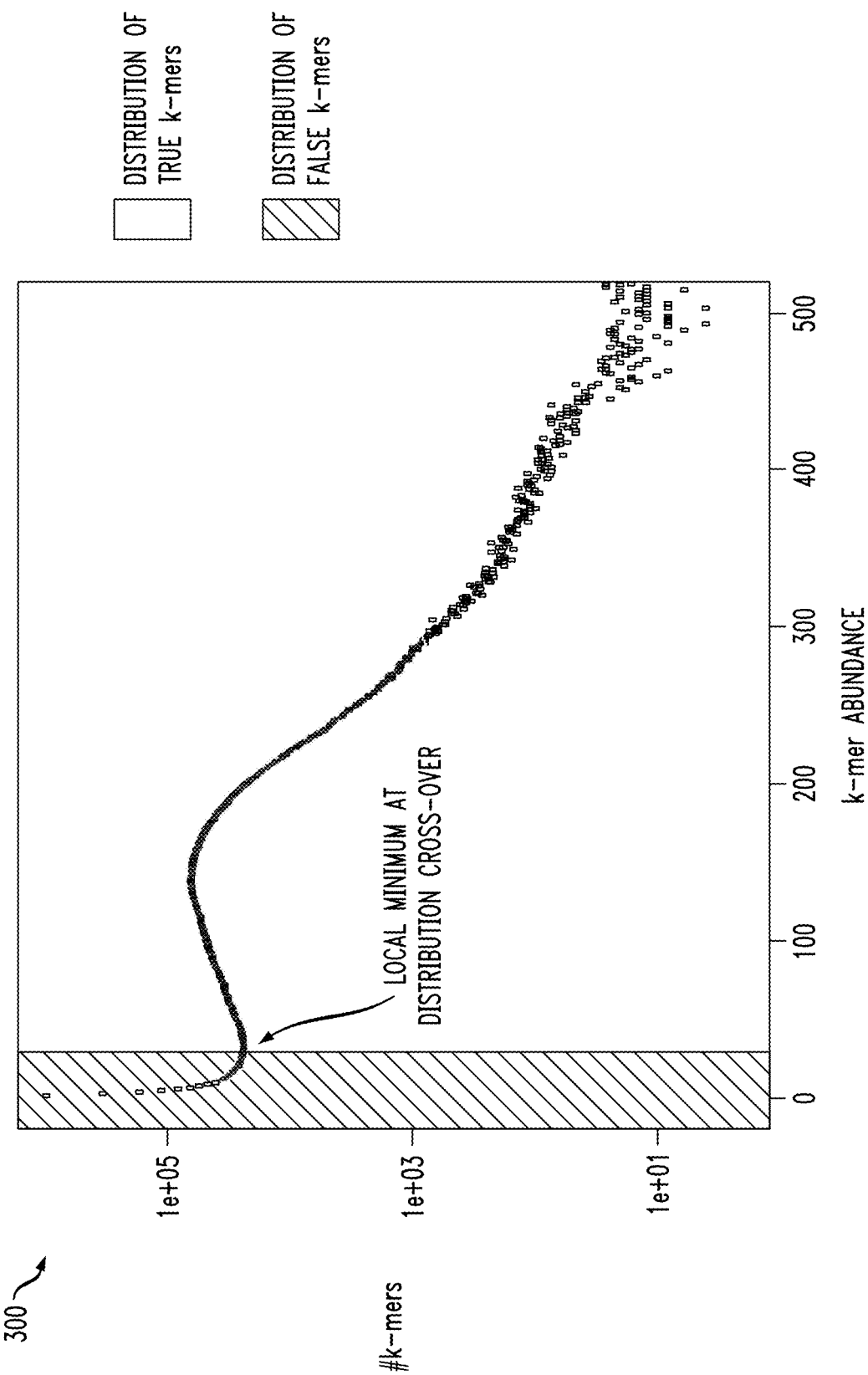
FIG. 3 illustrates an example of a k-mer frequency distribution with which one or more embodiments of the invention may be implemented.

MLVA and MLST techniques characterize individuals based on genetic variation across multiple loci, which are dispersed around the genome, as will be further explained below in the context of FIG. 1. The MLVA technique involves characterization of the locus by inference of the number of tandem copies of a given DNA sequence repeat motif e.g., the triplet "ATT." Conventional MLVA techniques are described in well-known technical literature, for example, see P. Keim et al., "Multiple-Locus Variable-Number Tandem Repeat Analysis Reveals Genetic Relationships Within *Bacillus anthracis*," J. Bacteriol., 182:2928-2936, 2000. The MLST technique involves characterization of the locus by inference of the exact DNA sequence (called an allele) over a specific region (typically about 400-500 bases in length). Conventional MLST techniques are described in well-known technical literature, for example, see M. C. J. Maiden et al., "Multilocus Sequence Typing: A Portable Approach to the Identification of Clones Within Populations of Pathogenic Microorganisms," Proc. Natl. Acad. Sci., USA, 95:3140-3145, 1998. The MLVA type is the list of integers representing the copy number at each locus. Note that the repeat motifs are not identical for each locus. Additionally, repeats may be inexact, e.g., nine of ten copies at a locus could be "ATT" and the remaining copy could be "GTT." The existing laboratory based technique may infer the copy number from the total length of the tandem repeat.

In contrast, MLST is an exact matching technique where each distinct DNA sequence at a locus is assigned a distinct allele number (where alleles describe sequence variants at a given locus). Subsequently, each distinct combination of allele numbers, known as an "allelic profile," is assigned a distinct sequence type (ST). Allele sequences and profiles for the standard MLST schemes can be queried in the international MLST databases (e.g., www.pubmlst.org and www.mlst.net). Like MLVA, MLST schemes are generally species-specific and for some species there are multiple international schemes.

MLVA and MLST techniques are useful for determining the genetic relatedness of individuals and allow observation of epidemiological trends.

FIG. 1 illustrates an MLVA technique and an MLST technique. Circles on the left represent bacterial chromosomes and letters indicate the relative positions of loci included in the MLVA (upper or reference numeral 100) and MLST (lower or reference numeral 110) schemes. Note MLVA locus A is different from MLST locus A, MLVA locus B is different from MLST locus B, etc. MLVA loci are defined by the number of copies of a specified tandem repeat motif e.g., "ACT" as shown in underline for MLVA locus A (upper center) (SEQ ID NO. 4; SEQ ID NO. 5 and SEQ ID NO. 6). Repeat copy counts for all loci are combined to define the MLVA type, as shown in the upper right box. MLST loci are defined by their distinct DNA sequence and numbered sequentially in the (arbitrary) order of discovery/curation, e.g., as shown for MLST locus A (lower center—for convenience, underlined text highlights variable positions) (SEQ ID NO. 7; SEQ ID NO. 8 and SEQ ID NO. 9). Distinct combinations of allele numbers are assigned distinct STs, numbered sequentially in the (arbitrary) order of discovery/curation, as shown in the lower right box.

The conventional way of performing MLVA is to use experimental laboratory techniques comprising the polymerase chain reaction (PCR) to generate multiple copies of ("amplify") selected regions of the DNA from a purified microorganism sample (known as an "isolate"). The sequence copies generated during the PCR reaction are known as "amplicons" and are subjected to electrophoresis to determine their lengths, or by targeted sequencing (usually capillary-based Sanger sequencing). The number of tandem repeat motif copies can be calculated from the length or the amplicon or sequence. The process is completed for each MLVA locus as defined in the species-specific reference scheme.

The conventional way of performing MLST is to use PCR to amplify the loci of interest, followed by targeted sequencing (usually capillary-based Sanger sequencing at two times (2×) coverage). However, it is realized here that these conventional techniques are becoming increasingly redundant given the recent advent of next-generation sequencing (NGS) platforms, which enable DNA sequence data to be collected cheaply and at an unprecedented scale, without the need to select and target specific sequence regions. For a description of example NGS technologies, see M. L. Metzker, "Sequencing Technologies—the Next Generation," Nat. Rev. Genet., 11:31-46, 2010.

As generally applied, NGS technologies (also known as, e.g., "high-throughput sequencing," or for the newest generation, "third generation sequencing") generate large numbers (usually millions) of typically short, overlapping sequence reads at greater than two times (>2×) coverage (i.e., each base of the sample sequence is sampled >2×). FIG. 2 illustrates an example of next-generation sequence sampling. The true sample sequence is represented in the shaded box 200 (SEQ ID NO. 10). Sequence reads (e.g., 210 in FIG. 2; (SEQ ID NO. 11) represent overlapping regions of the true sequence. Each base of the true sequence is sampled (sequenced) multiple times, the extent of which is known as "coverage depth" (e.g., 220 in FIG. 2). The true coverage depth varies across the sample sequence and is often approximated as an average. Underlined text indicates sequencing errors where the base represented in the sequence read is different from that in the relevant region of the true sequence. This type of error is known as a "substitution."

Each true read represents a fragment of the true sequence in the sample, which may be DNA, RNA or rtDNA (recombinant DNA). In the case of a DNA sequence, the true sequence may represent the complete genome of a single individual, a composite of genomes of multiple individuals or specific amplified region(s) of DNA from one or multiple individuals. When the technique is applied to a purified sample representing the complete genome of a single individual, it may also be called "whole-genome sequencing." In this case, the sequencing protocols are generally designed such that sequence reads represent regions that are approximately randomly distributed across the genome. In the case of bacterial genomes, the per base coverage is usually in the region of 10-100×.

Regardless of the type of sample, there may be known relationships within the set of sequence reads e.g., some sequencing equipment can produce data in which pairs of sequences are read from the ends of a single DNA fragment, or the sequencing may have been done in such a way as to ensure that all the sequences come from a single strand of double-stranded DNA.

In silico derivation of existing assays from NGS data is an important area of research and development, and is essential to enable compatibility between data sources. For MLVA in particular, no NGS based method exists to reliably derive the typing information (repeat motif numbers/amplicon lengths at each locus of interest).

In contrast, there have been multiple strategies proposed to derive MLST information from NGS data. Previous approaches fall into two categories: mapping based approaches and assembly based approaches. Mapping based approaches proceed by mapping or aligning the comparatively short NGS reads to a set of reference sequences and analyzing the results to determine which allele is present at each locus. Assembly based approaches reconstruct the underlying genome by piecing together overlapping reads, then analyze the results to determine which alleles are present (e.g., by the Basic Local Alignment Search Tool (BLAST) and sequence alignment). The existing approaches perform general analysis procedures (mapping or assembly) then extract the sequence type information from the results of those general procedures.

Illustrative embodiments of the invention provide computational methods related to the identification of signatures from comparatively short, overlapping sequences obtained from a biological sample. The source data from which a signature is to be deduced are comprised of one or more sequences of, for example, DNA bases which are derived by some measurement technique from the biological sample. The input sequences may be individual sequence reads from a sequencing technology, or they may be the result of processing raw input sequences to combine or otherwise transform them. In the illustrative embodiments described here, a primary assumption is that each source sequence corresponds to a contiguous sequence in the biological sample.

The methods of the illustrative embodiments described here are based on k-mer techniques which differ from mapping based techniques. Mapping based methods proceed by first determining which position on a reference sequence best matches each sequence in the source data. By contrast, k-mer based methods generally proceed by collecting all the k-mers out of the source data, and then performing some kind of analysis on them, without explicitly matching the source sequences. Some k-mer methods extract k-mers out of reference sequences and use them to classify individual sequences in the source data, but like the mapping approaches, these tend to operate on one source sequence at a time.

K-mer Preparation

Illustrative embodiments provide methods for extracting two general kinds of genomic feature from a set of source sequences: (1) primer delimited tandem repeat sequences; and (2) exact alleles. Both feature types are extracted by use of k-mer techniques, where a k-mer is a k length substring from a sequence of length greater than or equal to k. The following processing steps are common to the extraction of both features.

The first part of the methods described for determining genomic signatures from sequence data extract the k-mers from the set of source sequences. For each sequence in the set, the k-mers at all the positions are determined. If the source sequences come from a double stranded source (such as whole-genome or other NGS DNA sequencing), then the reverse complement of each k-mer should also be considered. The k-mers are collated so that a determination can be made as to the number of times each k-mer occurred across the whole collection.

For example, given the DNA sequence AACGCTTACGA (SEQ ID NO. 3), and taking k=3, the list (in order of position) of k-mers that may be extracted is AAC, ACG, CGC, GCT, CTT, TTA, TAC, ACG, CGA, and the collated collection, including reverse complements is: <AAC,1>, <AAG,1>, <ACG,2>, <AGC,1>, <CGA,1>, <CGC, 1>, <CGT,2>, <CTT,1>, <GCG,1>, <GCT,1>, <GTA,1>, <GTT,1>, <TAA,1>, <TAC,1>, <TCG,1>, <TTA,1>.

It is typically (but not necessarily) the case that the source sequences may contain errors. Before the collated k-mers can be used to determine a genomic signature, k-mers arising from errors should be eliminated. This may be done in various ways, but two specific ways are described for illustrative purposes.

When DNA sequence data is generated by an NGS instrument, it is usual that enough sequences are determined that each position in the underlying sample sequence is covered by multiple fragments as illustrated in FIG. 2. As a consequence, k-mers will appear with a frequency proportional to the coverage depth.

Errors in the source sequences obtained from such instruments are approximately uniform-randomly distributed, so "false" k-mers that cover errors in source sequences will appear in the collated k-mers with lower associated frequency than "true" k-mers. It has been shown that a low frequency, assumed false k-mer can be corrected to a similar true k-mer (assumed so because of its higher frequency), see, e.g., P. Medvedev et al., "Error correction of high-throughput sequencing datasets with non-uniform coverage," Bioinformatics 27 (13):137-141, 2011. Alternatively, all low frequency k-mers can simply be discarded, which is more robust provided the coverage depth is sufficient.

Determining the threshold below which a k-mer should be considered false, or above which it should be considered true can be done by examining the distribution of k-mer frequencies. That is, the number of times each k-mer frequency appears may be determined. FIG. 3 shows a typical distribution (denoted by reference numeral 300) of k-mer frequencies. As can clearly be seen, the overall distribution is the composition of two component distributions. The left-hand (low frequency) component shows the distribution of false k-mers, and the right-hand component shows the distribution of true k-mers. The threshold should be set to minimize the number of false k-mers retained, and minimize the number of true k-mers discarded.

A simple but effective way of doing this is to find the first local minimum of the combined distribution (see arrow pointing to local minimum at distribution cross-over in FIG. 3). There may be some noise in the distribution, so the robustness of this technique may be improved by applying median filtering to the combined distribution.

Alternatively, a more precise estimate may be determined by performing parameter estimation to fit an analytic model to the empirical distribution. An example of such a model would use an exponential distribution for the false k-mers and a Poisson distribution for the true k-mers, and a parameter estimation method such as Maximum Entropy or Levenberg-Marquardt. By doing so, a more precise choice can be made with an estimated number of true k-mers discarded and an estimated number of false k-mers remaining. Moreover, it can also be estimated how well the model fits the actual distribution, and if there are problems with the source data, they may be identified by a poor correspondence between the analytic and empirical models.

A second, and complementary approach to identifying errors relies on interpreting the collated k-mers as a de Bruijn graph. Under such an interpretation, many of the false k-mers lie on short paths that branch off "true" paths. This method may be used to eliminate most errors that remain after discarding low frequency k-mers. One illustrative method for creating a de Bruijn graph is described in T. C. Conway et al., "Succinct Data Structures for Assembling Large Genomes," Bioinformatics, 27:479-486, 2011. Another method is described in P. E. Compeau et al., "How to Apply de Bruijn Graphs to Genome Assembly," National Biotechnology, 29:987-991, 2011.

After performing these or other error correction or elimination methods, the result is a set of k-mers that form a representation of the underlying sample sequence given by the set of source sequences.

As mentioned above, FIG. 3 illustrates an example of a k-mer frequency distribution. "K-mer abundance" represents the number of copies of each distinct k-mer, while "# k-mers" is the number of distinct k-mers that appear at the corresponding copy number. The distribution comprises that of the false k-mers, resulting from sequencing error (low frequency only) and that of the true k-mers, representing regions of the true sample sequence. The local frequency minimum at the point of cross-over between the distributions is marked.

Fast and Accurate MLVA from Short Reads

A methodology for fast and accurate MLVA from short reads will now be described in accordance with one or more illustrative embodiments. This first method concerns the characterization of primer delimited tandem sequence repeats, e.g., as forms the basis of genotyping techniques such as MLVA.

Figure 4:
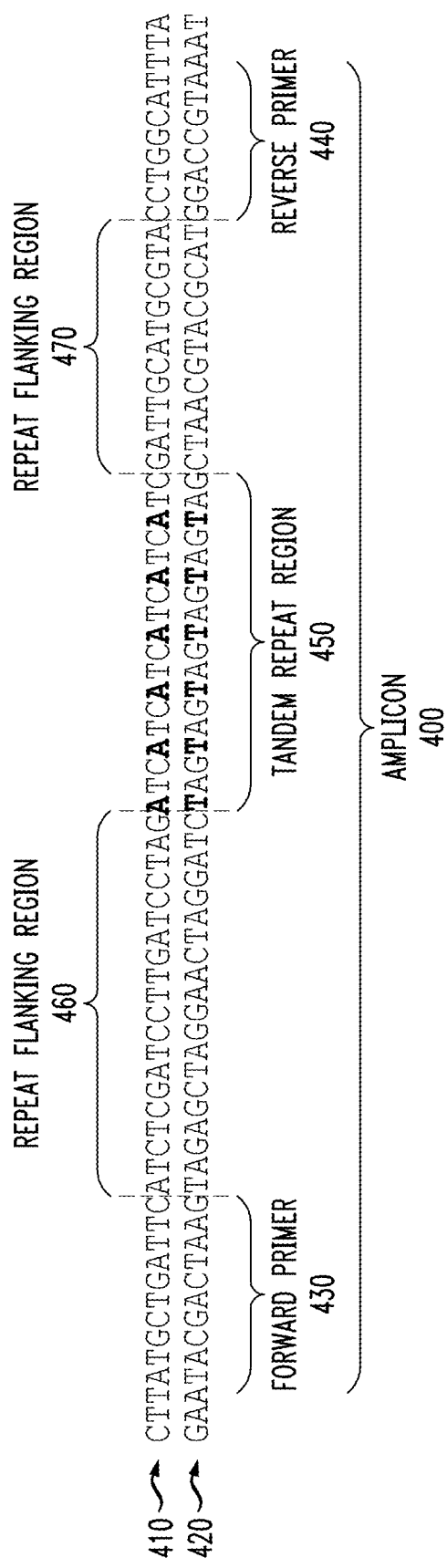
FIG. 4 illustrates a schematic representation of an MLVA amplicon in accordance with a biological sequence characterization methodology of one or more embodiments of the invention.

In such techniques, in addition to the source sequences, we have as an input the primer scheme. In the case of MLVA schemes, which are generally species-specific, each scheme is comprised of a series of locus definitions. Each locus is composed of the name of the locus, the variable length repeat motif and a pair of known primer sequences that flank (at some defined distance) the repeat region. The upstream primer is called the forward primer, and the downstream one is called the reverse primer, because under the traditional PCR-based method, they are designed to bind to the forward and reverse complementary DNA strands, respectively. The whole sequence from the start of the forward primer to the end of the reverse primer is equivalent to the PCR amplicon as illustrated in FIG. 4. That is, FIG. 4 is a schematic representation of an MLVA amplicon 400. The amplicon 400 spans the MLVA locus of interest (shown in the double stranded form where the upper line 410 represents the forward DNA strand (SEQ ID NO. 12) and the lower line 420 represents the reverse DNA strand (SEQ ID NO. 13)). The PCR primer binding sites (forward primer 430 and reverse primer 440) lie at the outer-most edges of the amplicon at a known distance from the tandem repeat motif region 450. The distances between the repeat regions (460 and 470) and each of the primers are specific to the MLVA locus in question such that the total number of repeat motif copies can be calculated when the total amplicon length, repeat flanking region lengths and repeat motif lengths are known.

In order to derive a characterization of the tandem repeat loci of interest from the NGS data, the methodology first processes the source sequences into k-mers as described above in k-mer preparation description. For each locus, the methodology then constructs a de Bruijn graph or other type of overlap graph starting with the sequence matching that of the first k-mer in the forward primer. Each k-mer represents an edge in the graph, and the nodes correspond to the k-1 length prefixes and suffixes. The methodology finds all possible paths through the graph that sequentially traverse the full set of k-mers matching those in the specified forward primer sequence, and continues to extend the path(s) until it reaches the sequence matching the reverse primer (as will be further described below in the context of FIG. 5).

If either or both of the primer sequences cannot be exactly matched, the methodology can chose to find low Hamming or Levinshtein distance matches. If there are no low Hamming or Levinshtein distance matches to either or both primers, or there is no path in the graph between them, then the sample is said to have a null allele—the locus does not occur in the sample.

In some cases, there is a simple non-branched path through the graph from the forward to the reverse primer sequences (or low Hamming or Levinshtein distance matches). This will occur if the repeat region is shorter than k, or the repeats are inexact. In these cases, there is a single possible sequence so the repeat region can be characterized directly from the graph. In the case of MLVA, the goal is to infer the number of repeat copies in the repeat region. When there is a simple non-branched path through the de Bruijn graph, or other overlap graph, the methodology can either scan the amplicon and count the number of instances of the repeat motif, or it can use the length of the flanks, the total length of the amplicon and the length of the repeat motif to compute the number of instances under the formula shown below or a suitable equivalent:

$$\frac{A - (P_1 + P_2 + F_1 + F_2)}{r} = n$$

Where n is the repeat motif copy number; A is the amplicon length; $P_1$ and $P_2$ are the lengths of the forward and reverse primer binding sites, respectively; $F_1$ and $F_2$ are the lengths of the upstream and downstream repeat flanking regions, respectively; r is the repeat motif length. (All lengths in bases.)

Figure 5:
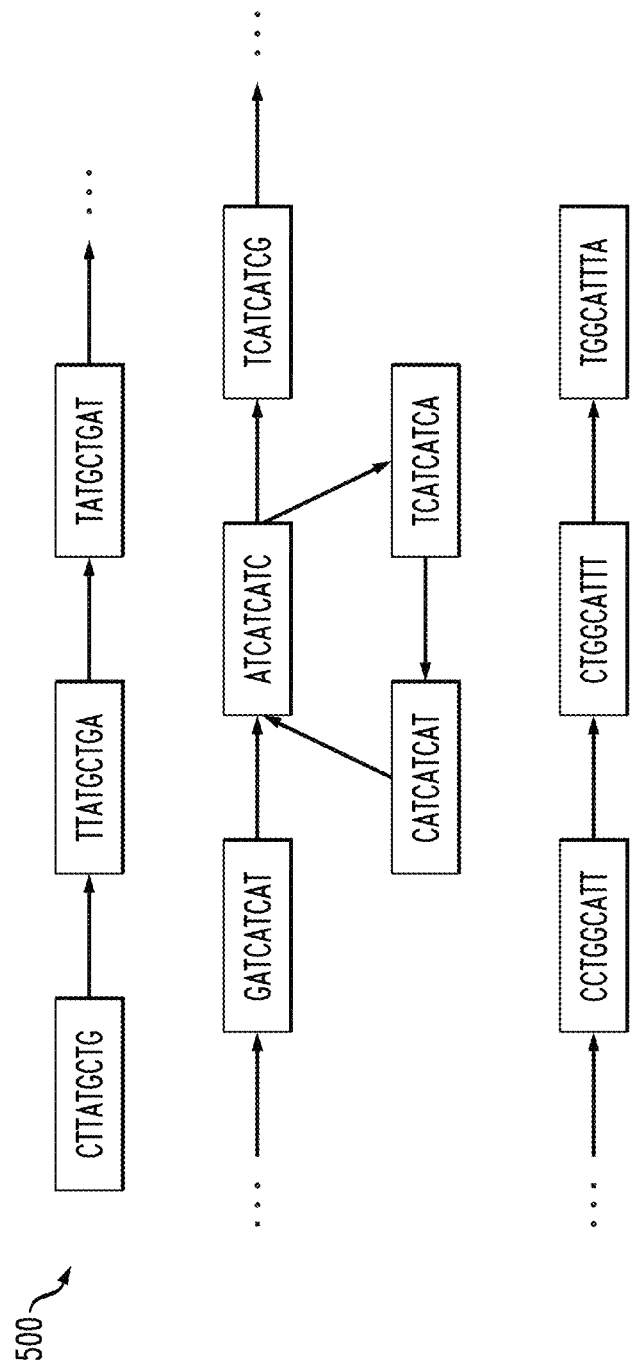
FIG. 5 illustrates a de Bruijn graph in accordance with a biological sequence characterization methodology of one or more embodiments of the invention.

In many cases, however, the repeat region forms a cycle in the de Bruijn graph, or other overlap graph, and it is not possible to directly compute the true path, because it is not clear how many times round the cycle the true path runs (see FIG. 5). In these cases, the methodology reprocesses the source reads looking for reads that completely span the repeat region (see FIG. 6). If the repeat region is longer than the read length, there is no direct evidence for the length of the repeat. A spanning read must have its first and last k-mers outside the cycle, but must pass through the cycle.

If the methodology is computing the copy number from amplicon length, the distribution of the number of times through a cycle each spanning read passes is defined. If the methodology is directly counting repeat copies, then the methodology can scan the read for this, and define the distribution. The reason for defining the distribution is that the DNA polymerase utilized during the NGS protocol sometimes slips over repeats so individual reads can sometimes yield different copy numbers (see FIG. 6). As such, a statistical test should be applied in order to estimate the true repeat copy number.

FIG. 5 illustrates an example of a de bruijn graph with cycle. The graph 500 represents the starting, ending and central regions of the path from the beginning to the end of the MLVA locus shown in FIGS. 4 and 6. The cycle representing the tandem repeat sequence region is shown.

Figure 6:
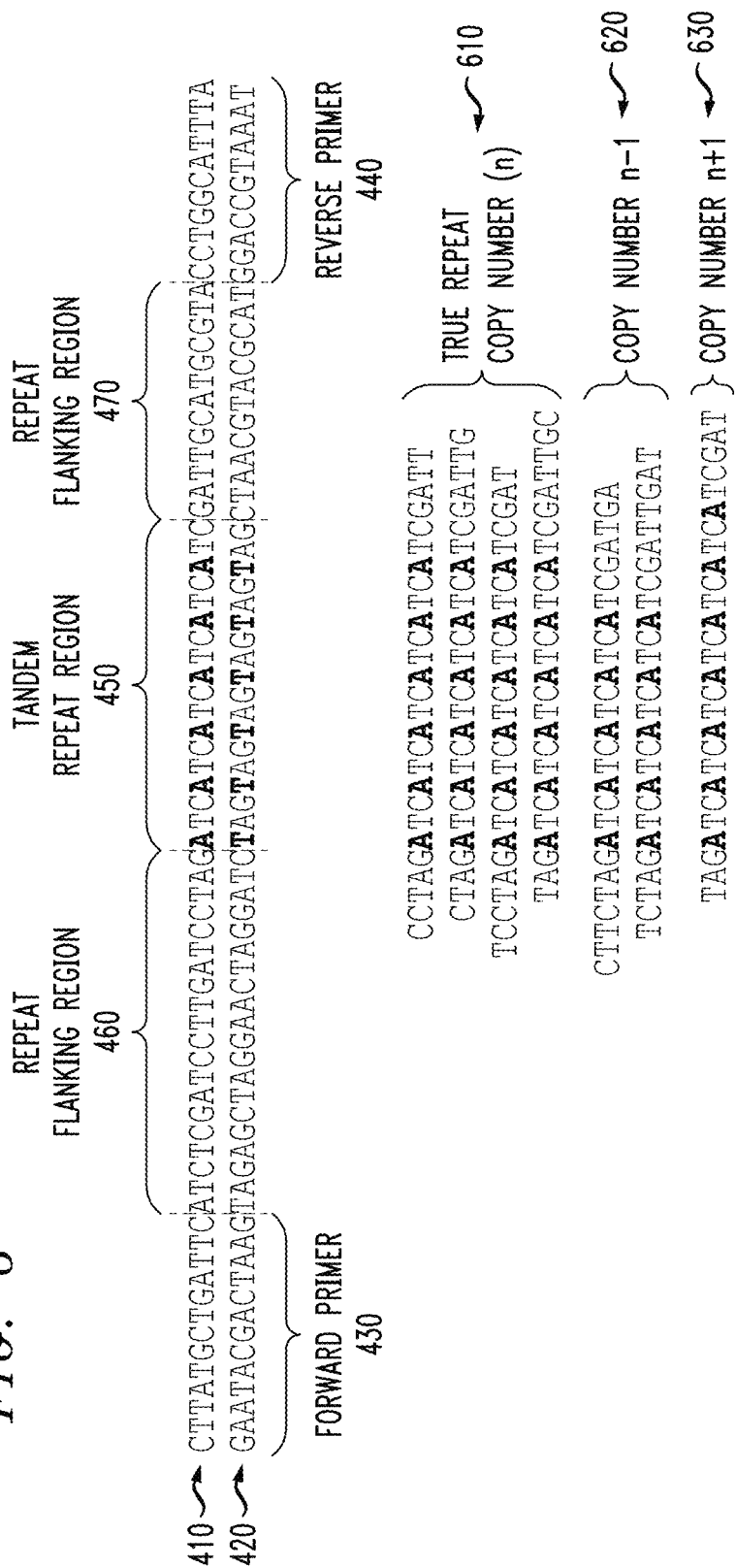
FIG. 6 illustrates sequence reads spanning an MLVA locus repeat region in accordance with a biological sequence characterization methodology of one or more embodiments of the invention.

FIG. 6 illustrates examples of sequence reads spanning the MLVA locus repeat region. The true sample sequence is shown (top) as in FIG. 4 (shown in the double stranded form where the upper line 410 represents the forward DNA strand (SEQ ID NO. 12) and the lower line 420 represents the reverse DNA strand (SEQ ID NO. 13) with primer binding sites 430 and 440, repeat region 450, and repeat flanking regions 460 and 470. Example sequence reads n (610), n−1 (620), and n+1 (630) spanning the repeat region are shown below the true sample sequence (read length=27 bases). The first and last k-mer of each read must fall outside of the repeat region. In this example, k=3 for illustrative purposes only (in practice larger values of k are used to prevent noise/crosstalk with reads representing other regions of the sample sequence). In some cases, the reads do not contain the correct number of repeat copies due to slippage of the polymerase enzyme during the sequencing reaction.

Accordingly, in one or more illustrative embodiments, a computational method for determining a signature from a biological sequence based on the length of repetitive sub-sequences and/or the number of copies of sub-sequence repeat motifs, from biological sequence data comprises the following steps. The biological sequence regions whose length is to be determined and/or which contains the repeat motif copies to be counted, are identified by flanking reference sequences (pre- and post-) which serve as markers, and where there may be extra sequence "letters" between the marker sequence and the repetitive sequence to be measured. Short fixed length sequences (source sub-sequences) are extracted from a collection of source sequences derived from a sample for which the signature is to be determined, and the extracted short fixed length source sub-sequences are compiled to determine the frequency of each within the collection. Frequency information and/or the overlap relationships between the short fixed length source sub-sequences may be used to eliminate short fixed length source sub-sequences that may be due to measurement error. The overlaps between the short fixed length source sub-sequences from the preceding step can be used to find a chain of overlaps from the sub-sequence(s) equivalent to the pre-flanking reference marker sequence to the sub-sequence(s) equivalent to the post-flanking reference marker sequence. Where the chain could contain multiple instances of any of the short fixed length source sub-sequences, that is a cycle, the sequences from the collection derived from the sample are examined to find any sequences that span the cycle, and: (i) use the lengths of the spanning sequences to determine the length of the cycle; and/or (ii) count the number of repeat motif copies within each spanning sequence. In sub-step (i) above, the length of the repetitive sequence region is determined by taking into account the distance between the reference marker sequence equivalents from the two preceding steps, and the number of extra sequence letters between the reference marker sequence equivalents and the repetitive sequence region. Furthermore, in one or more illustrative embodiments, the biological sequences are classified as, but not limited to, any of: DNA, RNA, and proteins. The sequence repeat regions may be known as, but are not limited to, tandem repeats, tandem repeat motif regions, and micro-satellites. The reference marker sequences may be known as primers. The short fixed length sub-sequences may be known as k-mers. The sample from which the source sub-sequences are derived may be one of, but are not limited to, whole-genome sequences, high-throughput sequences, whole-exome sequences, transcriptomes, and metagenomes. The chain of sub-sequence overlaps may take the form of a de Bruijn graph.

Fast and Efficient Method for MLST

A methodology for fast and efficient MLST will now be described in accordance with one or more illustrative embodiments. This second method concerns the identification of specific sequence variants within a biological sample. The identification of genomic allelic variants is relevant to genotyping schemes such as MLST, but is also applicable to any scheme for which a reference database of known alleles at one or more loci of interest is available. Thus, the method described herein is applicable to schemes other than MLST.

Figure 7:
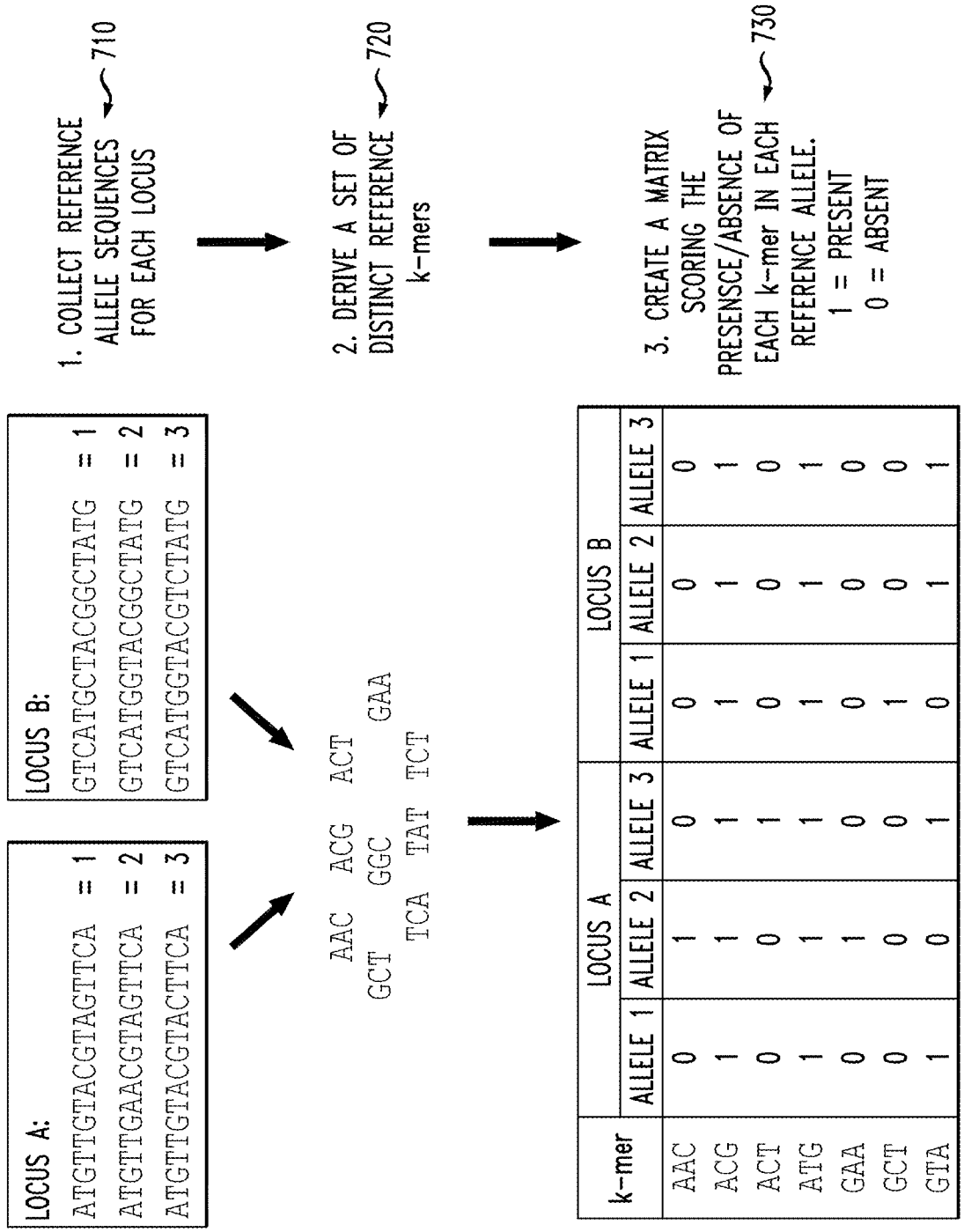
FIG. 7 illustrates construction of a reference k-mer matrix in accordance with a biological sequence characterization methodology of one or more embodiments of the invention.

In one illustrative embodiment, the method is an alignment-free method based on k-mers and utilizes the k-mer preparation techniques described above. The method first provides for the collection of reference alleles for each locus to be decomposed into reference k-mers and indexed to construct a matrix describing the alleles at each locus which contain that k-mer, an example of which is shown in FIG. 7, although other variations may also be applied. An important feature is that it is an index which shows for each k-mer in the collection of reference alleles, in which alleles, and possibly in which position within the allele, that k-mer occurs. In construction of this index, the method enables the determination of specific sequence variants of k≥1 length, and as such differs from that describing the use of single k-mer matching to determine the presence of a given sequence motif of k=1 length e.g., as described for the derivation of spoligotyping information from NGS data.

Thus, FIG. 7 shows an example method 700 for construction of the reference k-mer matrix set forth as LOCUS A (SEQ ID NO. 14; SEQ ID NO. 15 and SEQ ID NO. 16) and LOCUS B SEQ ID NO. 17; SEQ ID NO. 18 and SEQ ID NO. 19). In step 710, reference alleles are collected for each locus. In step 720, reference alleles at each locus are decomposed into distinct k-mers (e.g., k=3 for convenience here). In step 730, a matrix describing the presence and absence of each distinct k-mer in each reference allele sequence at each locus is generated. In this example, "1" indicates the presence of a k-mer, while "0" indicates its absence. For convenience, only three reference alleles at two distinct loci are shown. Steps of method 700 will now be described in further detail.

To analyze a collection of source sequences, each read (or read pair, in the case of paired end sequencing) is decomposed into k-mers as described above (k-mer preparation), and an orientation for the read (or pair) is chosen by examining whether there are more forward direction or reverse-complement k-mers in the read which are also present in the reference collection. For each k-mer from the reads which also occurs in the reference collection, the number of instances is counted. Once all the reads have been processed, we have a sample-specific k-mer frequency for each reference k-mer.

To determine which allele is present in the true sample sequence for each locus, the method first discards any reference allele for which at least one of its corresponding reference k-mers was identified in the sample at a frequency below a user specified minimum threshold (e.g., 5). Any such allele can be said to be insufficiently supported by the k-mer evidence. The remaining alleles are evaluated with a statistical hypothesis test against a null model that the frequency of k-mers is due to noise/crosstalk with sequence reads representing other regions of the sample sequence (i.e., not the locus of interest). Reference alleles that are judged insignificant are discarded.

Alternatively, if the source sequences were processed and putative error sequences removed, as described above in k-mer preparation, the list of true k-mers can be directly compared against the list of reference k-mers, and the reference index can be used as above to determine which alleles are supported by the set of source sequences. Given that the global processing of the source k-mers is used to determine which are true and which are false, the minimum depth threshold used above is not needed as part of the allele calling process.

All remaining alleles for a locus are judged either to be present in the true sample sequences or to be unresolvable. In practice, if the sample was thought to represent the genome of a single purified haploid organism (e.g., a bacterial isolate) but there are multiple alleles present, it usually means that there was contamination (i.e., biological material from one or more individual organisms additional to the individual of interest, was contained within the sample). In such cases, either the user can opt to pick the allele with the lowest statistical p-value (probability of making a type I statistical error), or report all candidates. As such, this method can be used to detect contamination among supposedly purified haploid organism samples.

By leveraging other information about the sample sequences, e.g., paired sequence read information or Hi-C information if available, the method can be extended to: (1) enable resolution of alleles at heterozygous loci in samples representing diploid organisms; and/or (2) separate alleles originating from different individuals among meta-genomic samples.

Figure 8:
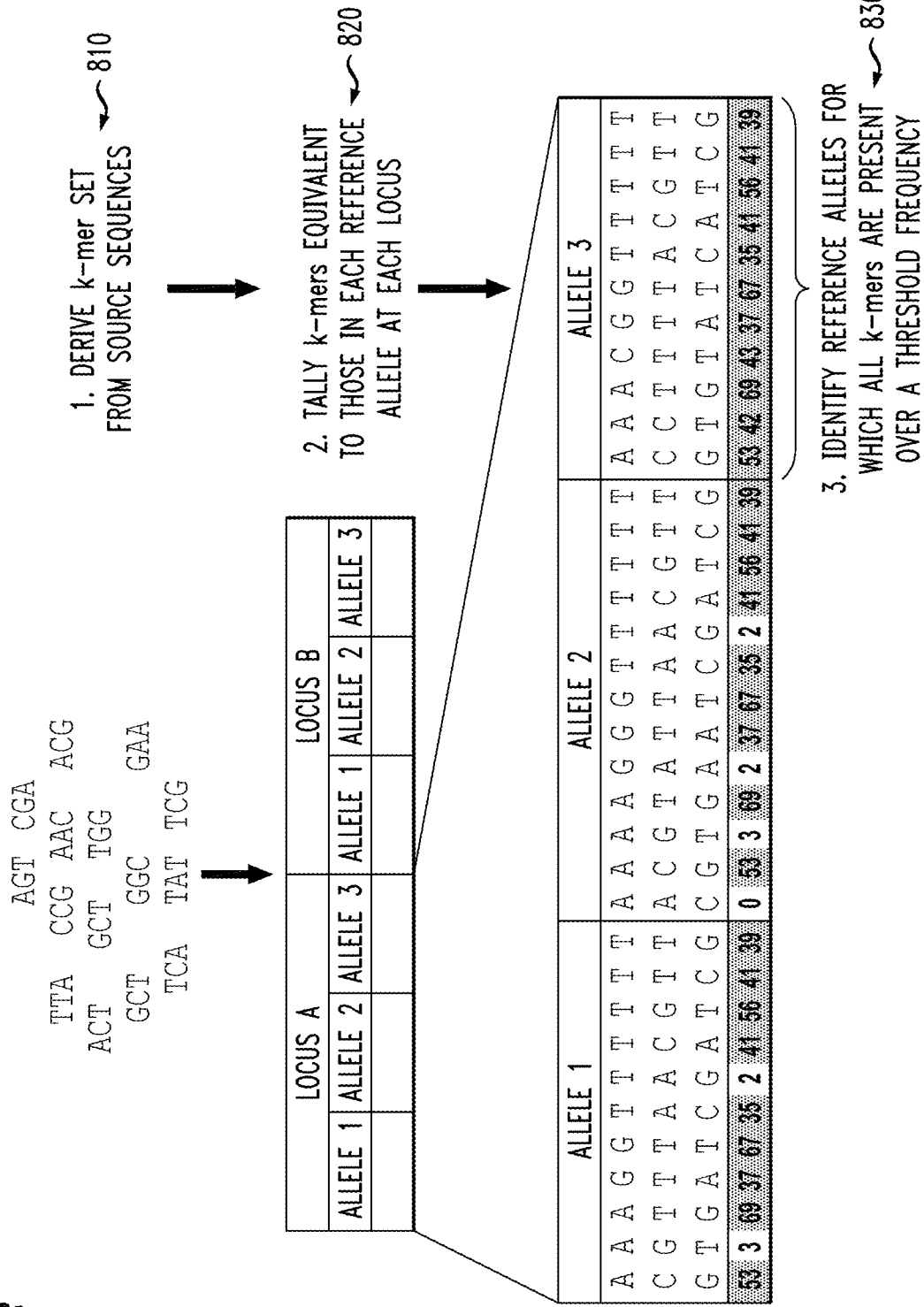
FIG. 8 illustrates identification of reference alleles in accordance with a biological sequence characterization methodology of one or more embodiments of the invention.

FIG. 8 illustrates a method for identification of reference alleles for which all k-mers are present in the sample over the minimum cut-off frequency threshold. In step 810, a k-mer set is derived from source sequences. In step 820, k-mers equivalent to those in each reference allele at each locus are tallied. In step 830, reference alleles for which all k-mers are present over a threshold frequency are identified, e.g., ALLELE 1 (SEQ ID NO. 20), ALLELE 2 (SEQ ID NO. 21) and ALLELE 3 (SEQ ID NO. 22).

That is, source sequence k-mers are compared to those in the reference k-mer matrix to determine the frequency of each reference k-mer in the source sequences. A second matrix describing the frequency of k-mers in the sample matching those in each reference allele at each locus is generated, and may take the form of that shown at the bottom of FIG. 8. Source sequence k-mer frequencies over the minimum threshold cut-off are shown in last line of the matrix in shading (frequency >5 in this example). Alleles for which all reference k-mers are present in the source sequences over the threshold frequency are identified and subjected to statistical assessment.

Furthermore, it is to be appreciated that if there are no candidate allele(s) for a locus, typically it will be either because there was insufficient data (e.g., the sequence coverage depth was too low), the sample contains a novel allele that was not included in the reference database, or the sample does not contain that locus, e.g., due to a genomic deletion. To determine the novel allele, the method uses a guided assembly.

The guided assembly is performed by selecting only those sample reads containing at least one reference k-mer in common with any existing reference allele. The full set of k-mers resulting from the k-mer decomposition of the selected source reads is considered. Low frequency k-mers are discarded since they are likely to represent sequencing errors as described above (see k-mer preparation). The remaining set of k-mers is treated as an order k de Bruijn graph, or other overlap graph. A unique path is then sought from a known initial reference k-mer (i.e., a k-mer starting at position 0 in any of the known reference alleles) to a known terminal reference k-mer (i.e., a k-mer present at the last position in any known reference allele). If either a known initial or terminal k-mer or both are not present in the graph, then a low Hamming or Levenshtein distance neighbor of a known reference k-mer is sought. This logic is applied since in many cases reference loci are chosen such that they start and end in regions of the genome that are conserved across individuals within a species (genus or sub-species).

If multiple paths through the de Bruijn graph or other overlap graph are present, then the alternatives are reported as candidate allele sequences. The candidate allele sequences are decomposed into candidate reference k-mers and scored in the same manner as known reference alleles so that a statistical test of significance can be applied as described above.

The method we describe is fast because extracting and manipulating k-mers (which are stored in single integer words—e.g., uint64_t) is very efficient. It is also fast because it does not compute alignments for individual sequence reads. At small values of k (e.g., <15), this would be a problem because of coincidental co-occurrence of k-mers across sequence reads representing different parts of the genome (i.e., not the loci of interest), but at the larger values that we use (e.g., 30), the degree of specificity is high and crosstalk is not a problem.

In comparison to non-targeted assembly techniques which seek to assemble the full complement of sequences in a sample (e.g., an entire genome), the targeted assembly is fast because it performs very fast cursory processing to select relevant reads, and then performs the more intensive (but still fast) assembly just on the relevant ones. For a single bacterial MLST locus, this results in a reduction of assembly sequence length by approximately four orders of magnitude.

Accordingly, in one or more illustrative embodiments, a computational method for determining a signature from biological sequence data comprises the following steps. Short fixed length sub-sequences (reference sub-sequences) are extracted from a collection of reference sequences, which may be composed of distinct subsets of reference sequences, and an index is constructed showing which short fixed length reference sub-sequence occurs in which reference sequences and, if desired, at which position. Short fixed length sub-sequences (the same length as the reference sub-sequences in the above step, and referred to as source sub-sequences) are extracted from a collection of source sequences derived from a sample for which the signature is to be determined, and those short fixed length source sub-sequences are compiled to determine the frequency of each within the collection. The frequency information and/or the overlap relationships between the short fixed length source sub-sequences may be used to eliminate short fixed length source sub-sequences that may be due to measurement error. The presence or absence of short fixed length source sub-sequences from the results of the preceding step in combination with the constructed index are used to infer the presence or absence of reference sequences with respect to the reference collection. Where a member of a subset of the reference collection is expected but not found to be present in the preceding step, the initial and final short fixed length reference sub-sequences of the members of the subset of reference sequence are used, along with the overlaps between the short fixed length source sub-sequences, to derive a novel member of that subset of the reference sequences. Furthermore, in one or more illustrative embodiments, the biological sequences are classified as, but not limited to, any of: DNA, RNA, and proteins. The short fixed length sub-sequences may be known as k-mers. The sample from which the source sub-sequences are derived may be one of, but are not limited to, next-generation sequences, whole-genome sequences, whole-exome sequences, transcriptomes, and metageomes. The reference sequence collection may include, but is not limited to, allelic (geno) typing schemes, e.g., multi-locus sequence typing or whole-genome sequence typing. Sub-sequence overlaps from which novel sequence variants are identified may take the form of a de Bruijn graph.

System and Computing Platform

Figure 9:
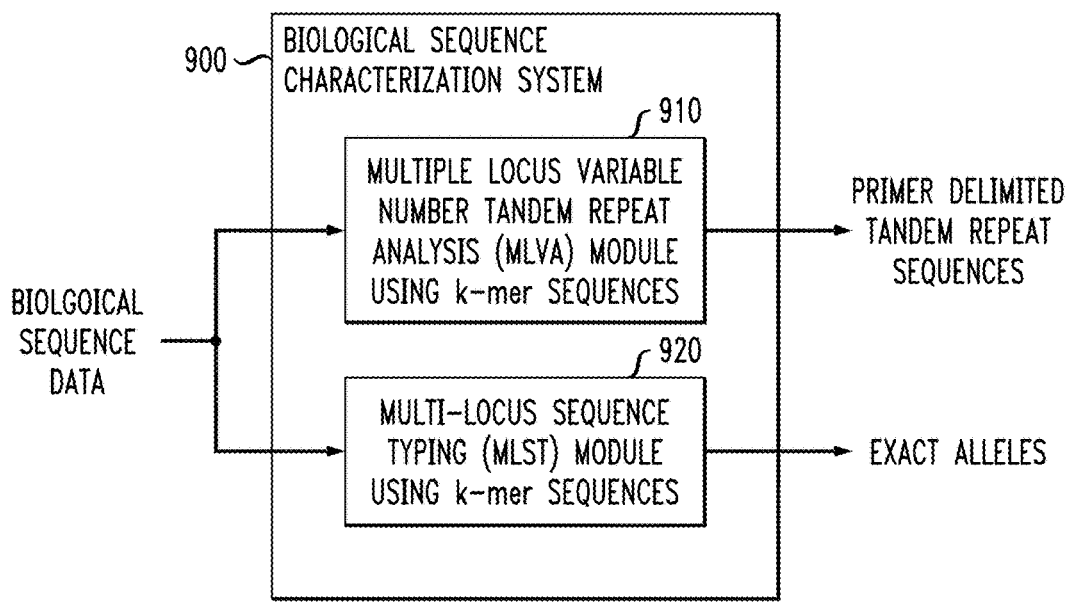
FIG. 9 illustrates a biological sequence characterization system in accordance with one or more embodiments of the invention.

FIG. 9 illustrates a biological sequence characterization system 900. As shown, system 900 includes two main modules: module 910 which is configured to perform MLVA using k-mer sequences; and module 920 which is configured to perform MLST using k-mer sequences. More particularly, module 910 is configured to extract a biological signature, in the form of primer delimited tandem repeat sequences, from input biological sequence data using one or more of the techniques described above in the context of FIGS. 4-6. Further, module 920 is configured to extract a biological signature, in the form of exact alleles, from input biological sequence data using one or more of the techniques described above in the context of FIGS. 7 and 8. Variations of these modules may be realized as explained above in the context of the various embodiments presented. Also, while system 900 is illustrated with modules 910 and 920 collocated in the same system, it is to be appreciated that each module, as well as parts thereof, can be implemented in a distributed manner across multiple systems and/or sub-systems.

Embodiments of the present invention may be a system, a method, and/or a computer program product. The computer program product may include a computer readable storage medium (or media) having computer readable program instructions thereon for causing a processor to carry out aspects of the present invention.

Figure 10:
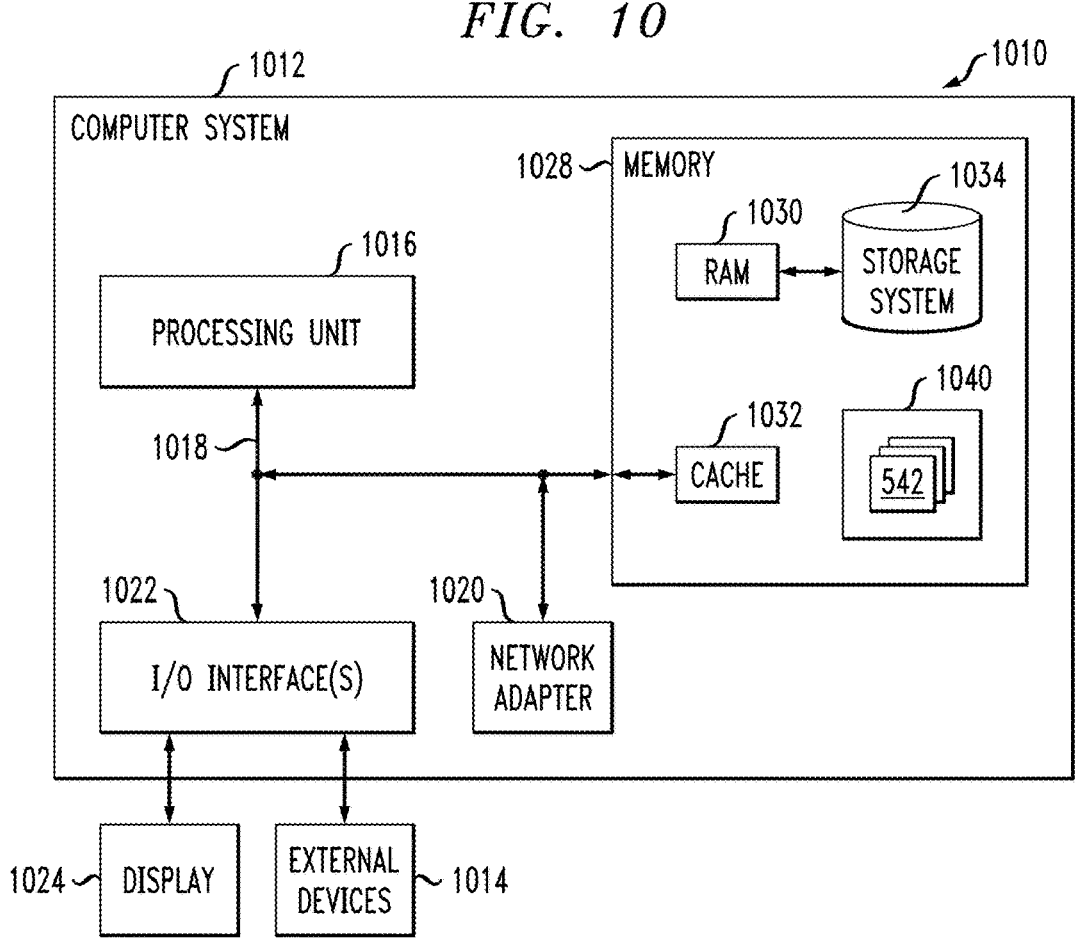
FIG. 10 illustrates a computing platform on which biological sequence characterization modules/steps are performed in accordance with one or more embodiments of the invention.

Accordingly, the architecture shown in FIG. 10 may be used to implement the various components/steps shown and described above in the context of FIGS. 1-9.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One or more embodiments can make use of software running on a general-purpose computer or workstation. With reference to FIG. 10, in a computing node 1010 there is a computer system/server 1012, which is operational with numerous other general purpose or special purpose computing system environments or configurations. Examples of well-known computing systems, environments, and/or configurations that may be suitable for use with computer system/server 1012 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1012 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1012 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 1012 in computing node 1010 is shown in the form of a general-purpose computing device. The components of computer system/server 1012 may include, but are not limited to, one or more processors or processing units 1016, a system memory 1028, and a bus 1018 that couples various system components including system memory 1028 to processor 1016.

The bus 1018 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 1012 typically includes a variety of computer system readable media. Such media may be any available media that is accessible by computer system/server 1012, and it includes both volatile and non-volatile media, removable and non-removable media.

The system memory 1028 can include computer system readable media in the form of volatile memory, such as random access memory (RAM) 1030 and/or cache memory 1032. The computer system/server 1012 may further include other removable/non-removable, volatile/nonvolatile computer system storage media. By way of example only, storage system 1034 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 1018 by one or more data media interfaces. As depicted and described herein, the memory 1028 may include at least one program product having a set (e.g., at least one) of program modules that are configured to carry out the functions of embodiments of the invention.

A program/utility 1040, having a set (at least one) of program modules 1042, may be stored in memory 1028 by way of example, and not limitation, as well as an operating system, one or more application programs, other program modules, and program data. Each of the operating system, one or more application programs, other program modules, and program data or some combination thereof, may include an implementation of a networking environment. Program modules 1042 generally carry out the functions and/or methodologies of embodiments of the invention as described herein.

Computer system/server 1012 may also communicate with one or more external devices 1014 such as a keyboard, a pointing device, a display 1024, etc., one or more devices that enable a user to interact with computer system/server 1012, and/or any devices (e.g., network card, modem, etc.) that enable computer system/server 1012 to communicate with one or more other computing devices. Such communication can occur via Input/Output (I/O) interfaces 1022. Still yet, computer system/server 1012 can communicate with one or more networks such as a local area network (LAN), a general wide area network (WAN), and/or a public network (e.g., the Internet) via network adapter 1020. As depicted, network adapter 1020 communicates with the other components of computer system/server 1012 via bus 1018. It should be understood that although not shown, other hardware and/or software components could be used in conjunction with computer system/server 1012. Examples include, but are not limited to, microcode, device drivers, redundant processing units, external disk drive arrays, RAID systems, tape drives, and data archival storage systems, etc.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. An article of manufacture comprising a computer readable storage medium for storing computer readable program code which, when executed, causes a computer node to perform the steps of:

receiving source biological sequence data comprising a collection of source sequences derived from an unknown biological sample, wherein the collection of source sequences derived from the unknown biological sample comprises a plurality of overlapping sequence reads providing greater than two times coverage of each of a plurality of bases of at least one genome in the source biological sequence data;

extracting short fixed length sub-sequences, defined as reference sub-sequences, from a collection of reference sequences derived from a reference biological sample;

constructing an index showing which short fixed length reference sub-sequence occurs in which reference sequences of the reference biological sample;

extracting short fixed length sub-sequences, the same length as the reference sub-sequences and defined as source sub-sequences, from the collection of source sequences derived from the unknown biological sample;

compiling the short fixed length source sub-sequences to determine the frequency of each within the collection of source sequences derived from the unknown biological sample;

selecting at least a subset of the short fixed length source sub-sequences based at least in part on comparing (i) the determined frequency of the short fixed length source sub-sequences within the collection of source sequences derived from the unknown biological sample with (ii) matching short fixed length reference sub-sequences in the index of references sequences of the reference biological sample;

performing a targeted assembly of the source biological sequence data by:

generating an overlap graph utilizing the selected subset of the short fixed length source sub-sequences; and identifying at least one path from at least a first one of the reference sub-sequences corresponding to an initial position of at least one designated biological sequence variant to at least a second one of the reference sub-sequences corresponding to a terminal position of said at least one designated biological sequence variant; and determining that the unknown biological sample comprises said at least one designated biological sequence variant responsive to identifying said at least one path.

2. The article of manufacture of claim 1, further comprising:

setting a threshold frequency and a threshold overlap relationship; and determining whether a given one of the extracted short fixed length source sub-sequences is due to measurement error based at least in part on comparing: (i) a frequency of the given extracted short fixed length source sub-sequence with the threshold frequency; and (ii) overlap relationships between the given extracted short fixed length source and one or more other ones of the extracted short fixed length source sub-sequences with the threshold overlap relationship.

3. The article of manufacture of claim 1, wherein the source biological sequence data comprises at least one of DNA, RNA, and proteins.

4. The article of manufacture of claim 1, wherein the unknown biological sample from which the source sub-sequences are derived comprises one of next-generation sequences, high-throughput sequences, whole-genome sequences, whole-exome sequences, transcriptomes, and metagenomes.

5. The article of manufacture of claim 1, wherein the reference sequence collection comprises an allelic genotyping scheme.

6. The article of manufacture of claim 5, wherein the allelic genotyping scheme comprises one of a multi-locus sequence typing and whole-genome sequence typing.

7. A system comprising:
   a non-transitory processor readable storage medium configured to store executable instructions; and
   a processor device operatively coupled to the storage medium;
   the processor device being configured, in response to execution of the executable instructions:
       to receive source biological sequence data comprising a collection of source sequences derived from an unknown biological sample, wherein the collection of source sequences derived from the unknown biological sample comprises a plurality of overlapping sequence reads providing greater than two times coverage of each of a plurality of bases of at least one genome in the source biological sequence data;
       to extract short fixed length sub-sequences, defined as reference sub-sequences, from a collection of reference sequences derived from a reference biological sample;
       to construct an index showing which short fixed length reference sub-sequence occur in which reference sequences of the reference biological sample;
       to extract short fixed length sub-sequences, the same length as the reference sub-sequences and defined as source sub-sequences, from the collection of source sequences derived from the unknown biological sample;
       to compile the short fixed length source sub-sequences to determine the frequency of each within the collection of source sequences derived from the unknown biological sample;
       to select at least a subset of the short fixed length sub-sequences based at least in part on comparing (i) the determined frequency of the short fixed length source sub-sequences within the collection of source sequences derived from the unknown biological sample with (ii) matching short fixed length reference sub-sequences in the index of references sequences of the reference biological sample;
       to perform a targeted assembly of the source biological sequence data by:
           generating an overlap graph utilizing the selected subset of the short fixed length source sub-sequences; and
           identifying at least one path from at least a first one of the reference sub-sequences corresponding to an initial position of at least one designated biological sequence variant to at least a second one of the reference sub-sequences corresponding to a terminal position of said at least one designated biological sequence variant; and
           determining that the unknown biological sample comprises said at least one designated biological sequence variant responsive to identifying said at least one path.

8. The system of claim 7, wherein the processor is further configured, in response to execution of the executable instructions:
   to set a threshold frequency and a threshold overlap relationship; and
   to determine whether a given one of the extracted short fixed length source sub-sequences is due to measurement error based at least in part on comparing: (i) a frequency of the given extracted short fixed length source sub-sequence with the threshold frequency; and (ii) overlap relationships between the given extracted short fixed length source and one or more other ones of the extracted short fixed length source sub-sequences with the threshold overlap relationship.

9. The system of claim 7, wherein the unknown biological sample from which the source sub-sequences are derived comprises one of next-generation sequences, high-throughput sequences, whole-genome sequences, whole-exome sequences, transcriptomes, and metagenomes.

10. The system of claim 7, wherein the reference sequence collection comprises an allelic genotyping scheme.

11. The system of claim 7, wherein the reference sequence collection comprises an allelic genotyping scheme which comprises one of a multi-locus sequence typing and whole-genome sequence typing.

12. The system of claim 7, wherein the source biological sequence data comprises at least one of DNA, RNA, and proteins.

13. The article of manufacture of claim 1, wherein the short fixed length sub-sequences comprise k-mers, wherein a value of k is selected to reduce coincidental co-occurrence of k-mers across sequence reads of the unknown biological sample.

14. The system of claim 7, wherein the short fixed length sub-sequences comprise k-mers, wherein a value of k is selected to reduce coincidental co-occurrence of k-mers across sequence reads of the unknown biological sample.

15. The system of claim 7, wherein compiling the short fixed length source sub-sequences to determine the frequency of each within the collection of source sequences derived from the unknown biological sample comprises:
   for at least a given one of the source sequences derived from the unknown biological sample, determining a k-mer short fixed length sub-sequence at each position of the given source sequence;
   collating the determined k-mer short fixed length sub-sequences to determine a number of times each of the k-mer short fixed length sub-sequences occur in the given source sequence; and
   removing at least one of the k-mer short fixed length sub-sequences from consideration responsive to determining that said at least one k-mer short fixed length sub-sequence corresponds to a measurement error of the unknown biological sample.

16. The system of claim 15, wherein determining that said at least one k-mer short fixed length sub-sequence corresponds to a measurement error of the unknown biological sample comprises:

identifying a distribution of the frequencies of the collated k-mer short fixed length sub-sequences; and removing any k-mers having frequencies below a designated threshold frequency.

17. The system of claim 16, wherein the designated threshold frequency is determined by computing a first local minimum of the distribution of the frequencies of the collated k-mer short fixed length sub-sequences.

18. The system of claim 16, wherein the designated threshold frequency is determined by performing parameter estimation to fit an analytic model to the distribution of the frequencies of the collated k-mer short fixed length sub-sequences.

19. The system of claim 18, wherein the analytic model comprises an exponential distribution for false k-mer short fixed length sub-sequences corresponding to measurement errors, a Poisson distribution for true k-mer short fixed length sub-sequences, and the parameter estimation utilizes at least one of maximum entropy and Levenberg-Marquardt.

20. The system of claim 15, wherein determining that said at least one k-mer short fixed length sub-sequence corresponds to a measurement error of the unknown biological sample comprises interpreting the collated k-mer short fixed length sub-sequences utilizing a de Bruijn graph, where said at least one k-mer short fixed length sub-sequence corresponding to the measurement error is on a path in the de Bruijn graph with a length less than a designated threshold.

* * * * *